United States Patent
Libbus et al.

(10) Patent No.: US 7,548,780 B2
(45) Date of Patent: Jun. 16, 2009

(54) CELL THERAPY AND NEURAL STIMULATION FOR CARDIAC REPAIR

(75) Inventors: Imad Libbus, St. Paul, MN (US);
Jeffrey Ross, Roseville, MN (US);
Steven D. Girouard, Woodbury, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 141 days.

(21) Appl. No.: 11/063,170

(22) Filed: Feb. 22, 2005

(65) Prior Publication Data
US 2006/0190044 A1    Aug. 24, 2006

(51) Int. Cl.
*A61N 1/18* (2006.01)
(52) U.S. Cl. ............................... 607/3; 607/9
(58) Field of Classification Search ............ 607/3, 607/9, 46
See application file for complete search history.

(56) References Cited

U.S. PATENT DOCUMENTS

| | | | |
|---|---|---|---|
| 5,103,821 A | 4/1992 | King | |
| 5,130,141 A | 7/1992 | Law et al. | |
| 5,486,359 A | 1/1996 | Caplan et al. | |
| 5,543,318 A | 8/1996 | Smith et al. | |
| 5,580,779 A | 12/1996 | Smith et al. | |
| 5,876,708 A * | 3/1999 | Sachs | 424/93.1 |
| 6,090,622 A | 7/2000 | Gearhart et al. | |
| 6,178,349 B1 | 1/2001 | Kieval | |
| 6,245,566 B1 | 6/2001 | Gearhart et al. | |
| 6,272,377 B1 | 8/2001 | Sweeney et al. | |
| 6,400,982 B2 | 6/2002 | Sweeney et al. | |
| 6,436,672 B1 | 8/2002 | Tomlinson | |
| 6,468,985 B1 | 10/2002 | Huang | |
| 6,487,446 B1 * | 11/2002 | Hill et al. | 604/20 |
| 6,511,500 B1 | 1/2003 | Rahme | |
| 7,277,761 B2 * | 10/2007 | Shelchuk | 607/62 |
| 2002/0107553 A1 | 8/2002 | Hill et al. | |
| 2002/0110910 A1 | 8/2002 | Gwathmey et al. | |
| 2002/0124855 A1 * | 9/2002 | Chachques | 128/898 |
| 2002/0147329 A1 | 10/2002 | Luyten et al. | |
| 2003/0078629 A1 | 4/2003 | Chen | |
| 2004/0049235 A1 | 3/2004 | Deno et al. | |
| 2004/0158290 A1 | 8/2004 | Girouard et al. | |
| 2005/0192637 A1 | 9/2005 | Girouard et al. | |

FOREIGN PATENT DOCUMENTS

| | | |
|---|---|---|
| WO | WO-0057950 | 10/2000 |
| WO | WO-03015863 | 2/2003 |

OTHER PUBLICATIONS

Berne R M and Levy M N: Physiology 4th edition; 1998, Mosby, Inc., St. Louis, MO, pp. 379-380.*

Borovikova, L. V., "Vagus nerve stimulation attenuates the systemic inflammatory response to endotoxin", *Nature*, 405(6785), (May 25, 2000),458-62.

(Continued)

*Primary Examiner*—Carl H Layno
*Assistant Examiner*—Brian T Gedeon
(74) *Attorney, Agent, or Firm*—Schwegman, Lundberg & Woessner, P.A.

(57) ABSTRACT

A method and system to enhance cell, gene and/or cytokine therapy for cardiac repair in a mammal.

38 Claims, 3 Drawing Sheets

OTHER PUBLICATIONS

Capecchi, M. R., "High efficiency transformation by direct microinjection of DNA into cultured mammalian cells.", *Cell*, 22(2 Pt 2), (Nov. 1980),479-88.

Chu, G., "SV40 DNA transfection of cells in suspension: analysis of efficiency of transcription and translation of T-antigen.", *Gene*, 13(2), (Mar. 1981),197-202.

Cserjesi, P., "Myogenin induces the myocyte-specific enhancer binding factor MEF-2 independently of other muscle-specific gene products", *Mol Cell Biol*, 11(10), (Oct. 1991),4854-62.

Dhawan, J., "Tetracycline-regulated gene expression following direct gene transfer into mouse skeletal muscle", *Somat Cell Mol Genet.*, 21(4), (1995),233-40.

Felgner, P. L., "Lipofection: A highly efficient, lipid-mediated DNA-transfection procedure", *Proceedings of the National Academy of Sciences*, 84, Biochemistry,(Nov. 1987),pp. 7413-7417.

Graham, F. L., "A New Technique for the Assay of Infectivity of Human Adenovirus 5 DNA", *Virology*, 52, (1973),456-467.

Henning, R J., "Effects of autonomic nerve stimulation, asynchrony, and load on dP/dtmax and on dP/dtmin", *American Journal of Physiology*, 260(4 Pt 2), (Apr. 1991),H1290-8.

Jain, Mohit, "Cell therapy attenuates deleterious ventricular remodeling and improves cardiac performance after myocardial infarction", *Circulation*, 103(14), (Apr. 10, 2001),1920-1927.

Johnson, J. E., "Muscle creatine kinase sequence elements regulating skeletal and cardiac muscle expression in transgenic mice", *Mol Cell Biol.*, 9(8), (1989),3393-9.

Klein, T. M., "High-Velocity Microprojectiles for Delivering Nucleic Acids into Living Cells", *Nature*, 327, (1987),70-73.

Lathrop, D A., et al., "On the neural connection", *Journal of Cardiovascular Electrophysiology*, 12(7), (Jul. 2001),841-4.

Lewis, M., et al., "Vagus nerve stimulation decreases left ventricular contractility in vivo in the human and pig heart", *Journal of Physiology 534.2*, (2001),547-552.

Mader, S., "A steroid-inducible promoter for the controlled overexpression of cloned genes in eukaryotic cells", *Proc Natl Acad Sci USA*, 90(12), (1993),5603-7

Mannino, R. J., "Liposome mediated gene transfer.", *BioTechniques*, 6(7), (Jul.-Aug. 1988),682-90.

Murry, C. E., et al., "Skeletal myoblast transplantation for repair of myocardial necrosis", *J Clin Invest*, 98(11), (Dec. 1, 1996),2512-23.

Muscat, G. E., "Multiple 5'-flanking regions of the human alpha-skeletal actin gene synergistically modulate muscle-specific expression", *Mol Cell Biol*, 7(11), (1987),4089-99.

Pagani, F. D., et al., "Autologous skeletal myoblasts transplanted to ischemia-damaged myocardium in humans. Histological analysis of cell survival and differentiation", *J Am Coll Cardiol.*, 41(5), (Mar. 5, 2003),879-88.

Palermo, J., "Transgenic remodeling of the contractile apparatus in the mammalian heart", *Circ Res*, 78(3), (1996),504-9.

Pouzet, B., "Intramyocardial transplantation of autologous myoblasts: can tissue processing be optimized?", *Circulation*, 102(19 Suppl 3), (2000),III210-5.

Semenza, G. L., "Hypoxia-inducible nuclear factors bind to an enhancer element located 3' to the human erythropoietin gen", *Proc Natl Acad Sci USA*, 88(13), (1991),5680-4.

Semenza, G. L., "Transcriptional regulation of genes encoding glycolytic enzymes by hypoxia-inducible factor 1", *J Biol Chem*, 269(38), (1994),23757-63.

Shigekawa, K., "Electroporation of Eukaryotes and Prokaryotes: A General Approach to the Introduction of Macromolecules into Cells", *BioTechniques*, 6, (1988),742-751.

Shockett, P., "A modified tetracycline-regulated system provides autoregulatory, inducible gene expression in cultured cells and transgenic mice", *Proc Natl Acad Sci USA*, 92(14), (1995),6522-6.

Strauer, B. E., et al., "Repair of infarcted myocardium by autologous intracoronary mononuclear bone marrow cell transplantation in humans", *Circulation*, 106(15), (Oct. 8, 2002),1913-8.

Suzuki, Ken, "Cell Transplantation for the Treatment of Acute Myocardial Infarction Using Vascular Endothelial Growth Factor-Expressing Skeletal Myoblasts", *Circulation*; 104[suppl I], (2001),I-207-I-212.

Terracio, Louis, "Effects of Cyclic Mechanical Stimulation of the Cellular Components of the Heart: In Vitro." *In Vitro Cellullar & Develomental Biology*, 24(1), (Jan. 1988),53-58.

Tracey, K. J., "The inflammatory reflex", *Nature*, 420(6917), (Dec. 19-26, 2002),853-9.

Weintraub, H., "The myoD gene family: nodal point during specification of the muscle cell lineage", *Science*, 251(4995), (Feb. 15, 1991),761-6.

Zimmermann, W. H., et al., "Tissue engineering of a differentiated cardiac muscle construct", *Circulation Res*, 90(2), (Feb. 8, 2002),223-30.

\* cited by examiner

CELL THERAPY AND NEURAL STIMULATION FOR CARDIAC REPAIR

TECHNICAL FIELD

This application relates generally to implantable medical devices and, more particularly, to systems, devices and methods for cell therapy and neural stimulation for cardiac repair.

BACKGROUND

Implanting a chronic electrical stimulator, such as a cardiac stimulator or a neural stimulator, to deliver medical therapy (ies) is known. Examples of cardiac stimulators include implantable cardiac rhythm management (CRM) devices such as pacemakers, implantable cardiac defibrillators (ICDs), and implantable devices capable of performing pacing and defibrillating functions. Examples of neural stimulators include neural transducers, peripheral nerve stimulators, e.g., vagus nerve stimulators, and cortical stimulators.

One technique for providing artificial neural stimulation entails implanting an electrode into direct contact with a portion of a selected nerve to influence a baroreflex. A separate, battery-powered activation source or triggering device is likewise implanted and connected to the electrode. The electrode is periodically activated by the triggering device, thereby stimulating the nerve in question and prompting a baroreflex decrease in heart rate. Essentially, activation of the electrode serves to simulate a rise in blood pressure, causing the baroreflex reduction in heart rate.

CRM devices are implantable devices that provide electrical stimulation to selected chambers of the heart in order to treat disorders of cardiac rhythm. An implantable pacemaker, for example, is a CRM device that paces the heart with timed pacing pulses. If functioning properly, the pacemaker makes up for the heart's inability to pace itself at an appropriate rhythm in order to meet metabolic demand by enforcing a minimum heart rate. Some CRM devices synchronize pacing pulses delivered to different areas of the heart in order to coordinate the contractions. Coordinated contractions allow the heart to pump efficiently while providing sufficient cardiac output.

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease.

Following a myocardial infarction, myocytes in the infarcted region die and are replaced by scar tissue, which has different mechanical and elastic properties from functional myocardium. Over time, this infarcted area can thin and expand, causing a redistribution of myocardial stresses over the entire heart. Ventricular remodeling following a myocardial infarction frequently leads to impaired mechanical function and heart failure.

What is needed is an improved method for cardiac repair.

SUMMARY

The present invention provides methods and systems for providing neural stimulation to enhance cardiac repair and/or cardiac function in a mammal, such as the stimulation of one or more efferent parasympathetic nerves which innervate cardiac tissue, e.g., including nerves which innervate veins and arteries of the heart, e.g., carotid sinus or aortic arteries, and cardiac fat pads, which mammal is subjected to exogenous therapy, for instance, cell therapy, gene therapy and/or cytokine and/or drug therapy. The neural stimulation may occur prior to, during, following, or any combination thereof, the delivery (administration) of cell therapy, gene therapy and/or cytokine or other drug therapy. In one embodiment, the mammal, prior to receiving neural stimulation and exogenous therapy, has reduced cardiac function due to disease or an undesirable myocardial event including but not limited to ischemic heart disease, heart failure, or MI. The neural stimulation is effective to modulate cardiac contractility, reduce inflammation, and/or reduce mechanical loading in or near a region in need of cardiac repair or enhanced (increased or improved) cardiac function in the mammal, which in turn may create an environment more suited to survival, localization, implantation and/or proliferation of exogenously administered donor cells in cardiac tissue, e.g., in a region in need of repair or enhanced cardiac function, localization, implantation, and/or proliferation of endogenous cells, e.g., endogenous stem cells, in cardiac tissue, may enhance the efficacy of gene therapy, e.g., in cardiac tissue, due to, for instance, reduced inflammation in tissues including cardiac tissue, and/or may enhance the efficacy of cytokine or other drug therapy. In one embodiment, neural stimulation modulates the local inflammatory response, leading to enhanced localization of endogenous stem cells or exogenously administered donor cells in cardiac tissue, and/or enhanced integration and/or expression of gene therapy vectors. Once localized to cardiac tissue, endogenous stem cells or donor cells may secrete factors that enhance local angiogenesis.

Various aspects and embodiments of the invention use a parameter related to cardiac activity to automatically modulate electrical stimulation of efferent nerves which innervate cardiac tissue. The use of indices of cardiac activity allows an implantable neural stimulator to respond to changes in metabolic demand, e.g., after cell, cytokine, drug and/or gene therapy. In other embodiments, a predetermined electrical stimulation profile(s), e.g., a profile with lower stimulation of efferent nerves that is not based on cardiac activity, may be employed.

One embodiment of the invention relates to a system for providing electrical stimulation of efferent nerves which innervate cardiac tissue or arteries thereof. An embodiment of the system comprises a cardiac activity monitor to sense cardiac activity and provide a signal indicative of the cardiac activity, and an electrical stimulator. The stimulator includes a pulse generator and a modulator. The pulse generator provides an electrical stimulation signal adapted to provide electrical stimulation to a nerve. In one embodiment, the modulator receives a signal indicative of cardiac activity or inflammation and modulates the electrical stimulation signal to the nerve based on the signal to change the electrical stimulation from a first electrical stimulation profile to a second electrical stimulation profile. Another embodiment of the system includes a pulse generator to provide a predetermined electrical stimulation profile. In one embodiment, a predetermined electrical stimulation profile includes 5 to 150 Hz, 20 to 120 Hz or 20 to 50 Hz, with 5 to 15 second bursts, e.g., 5 to 10 second bursts/minute or 5 second bursts/30 seconds, including one which is not proportional to cardiac activity. Optionally, the electrical stimulation occurs at predetermined times, e.g., during and/or after cell therapy, gene therapy and/or cytokine and/or drug therapy.

The invention thus provides a method which includes applying electrical stimulation to an efferent parasympathetic nerve which innervates cardiac tissue including one or more cardiac fat pads in a mammal with impaired cardiac function or in need of cardiac repair and subjected to exogenous cell therapy comprising donor cells, gene therapy and/or cytokine and/or drug therapy. The neural stimulation is in an amount effective to modulate cardiac function including modulation of cardiac contractility, inhibit inflammation in cardiac tissue, reduce mechanical loading in cardiac tissue, reduce metabolic demand in cardiac tissue, and/or increase localization, survival, proliferation or differentiation of donor cells in cardiac tissue, enhance gene therapy and/or enhance cytokine therapy of the mammal. In one embodiment, a neural stimulation device is implanted before cell gene, cytokine and/or drug therapy. In one embodiment, the cytokine is administered intravenously. In one embodiment, the cytokine is G-CSF, SDF-1, HGF, or IGF. In one embodiment, the donor cells are hematopoietic stem cells, neural stem cells, bone marrow derived stem cells, SP cells, bone marrow cells or skeletal myoblasts. The donor cells may be autologous, xenogeneic or allogeneic cells. The donor cells may be genetically modified in vitro, or subjected to conditions in vitro, e.g., mechanical stresses or altered environmental conditions such as hypoxic conditions, prior to implantation.

Also provided is a method in which electrical therapy is applied using a lead to an efferent parasympathetic nerve which innervates cardiac tissue including one or more cardiac fat pads of a mammal subjected to exogenous cell therapy comprising donor cells, gene therapy and/or cytokine and/or drug therapy. A physiologic parameter indicative of cardiac contractility, inflammation, mechanical remodeling, and/or mechanical loading is sensed and the electrical therapy is modifying based on the sensed physiological parameter. In one embodiment, the donor cells are hematopoietic stem cells, neural stem cells, bone marrow derived stem cells, SP cells, bone marrow cells or skeletal myoblasts. The donor cells may be autologous, xenogeneic or allogeneic cells. The donor cells may be genetically modified in vitro, or subjected to conditions in vitro, e.g., mechanical stresses or altered environmental conditions such as hypoxic conditions, prior to implantation. The electrical stimulation may be before, after and/or during, or any combination thereof, cell, gene and/or cytokine and/or drug therapy.

In one embodiment, the invention provides a method for enhancing cell, gene and/or cytokine or other drug therapy in a mammal with impaired cardiac function or in need of cardiac repair. The method includes administering exogenous cell therapy comprising donor cells, gene therapy and/or cytokine or drug therapy to a mammal having a device which applies electrical stimulation to an efferent parasympathetic nerve which innervates cardiac tissue including one or more cardiac fat pads. The electrical stimulation is applied so as to modulate cardiac contractility, inhibit inflammation in cardiac tissue, reduce mechanical loading in cardiac tissue, and/or increase localization, survival, proliferation or differentiation of the donor cells in cardiac tissue, enhance gene therapy, and/or enhance cytokine or drug therapy, in the mammal.

In one embodiment of the invention, a method for operating an implantable medical device is provided. In an embodiment of the method, a signal regarding an activity level is received, and an electrical stimulation profile for the device is set based on the signal.

According to one embodiment, an activity level is determined, an electrical stimulation profile is set based on the activity level, and electrical stimulation is applied according to the profile.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

Figure 1A:
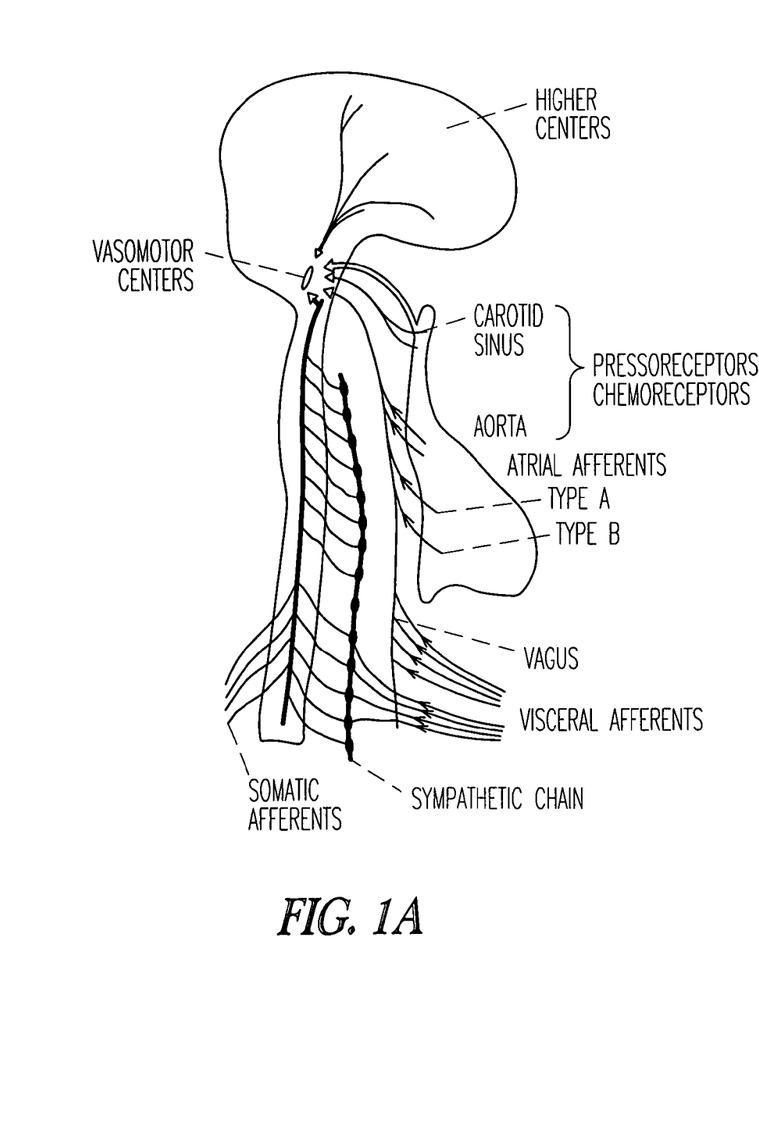
FIGS. 1A and 1B illustrate neural mechanisms for peripheral vascular control.
Figure 1B:
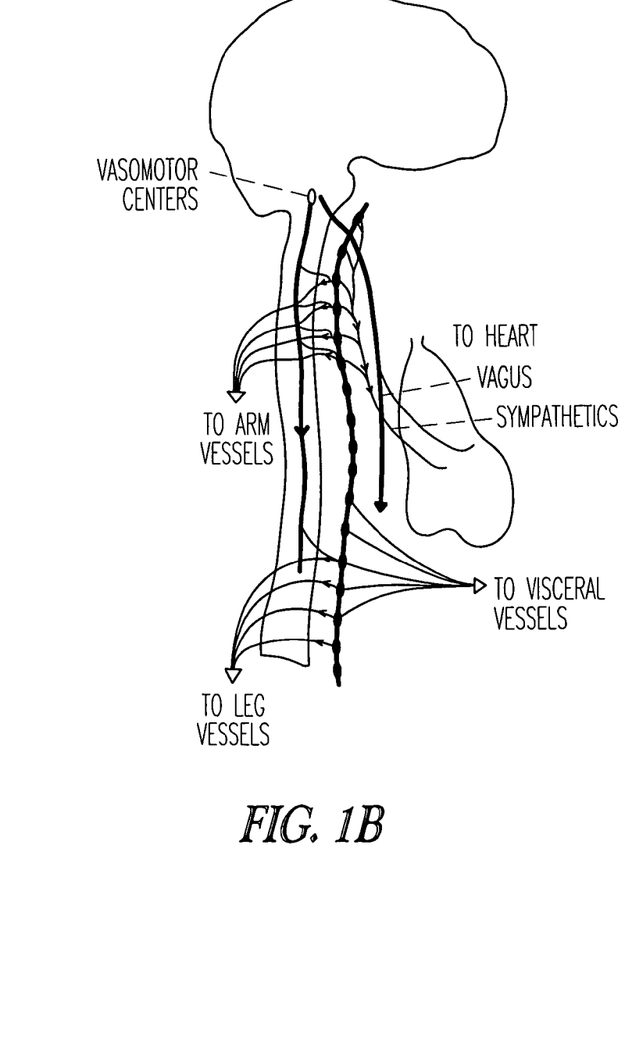

The heart rate and force is increased when the sympathetic nervous system is stimulated, and is decreased when the sympathetic nervous system is inhibited and the parasympathetic nervous system is stimulated. FIGS. 1A and 1B illustrate neural mechanisms for peripheral vascular control. FIG. 1A generally illustrates afferent nerves to vasomotor centers. An afferent nerve conveys impulses toward a nerve center. An example of a vasomotor center relates to nerves that dilate and constrict blood vessels to control the size of the blood vessels. FIG. 1B generally illustrates efferent nerves from vasomotor centers. An efferent nerve conveys impulses away from a nerve center.

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system and/or inhibiting the sympathetic nervous system constricts the pupil, increases saliva and mucus production, contracts the bronchial muscle, increases secretions and motility in the stomach and large intestine, and increases digestion in the small intestine, increases urine secretion, and contracts the wall and relaxes the sphincter of the bladder. The functions associated with the sympathetic and parasympathetic nervous systems are many and can be complexly integrated with each other. Thus, an indiscriminate stimulation of the sympathetic and/or parasympathetic nervous systems to achieve a desired response in one physiological system may also result in an undesired response in other physiological systems.

Some aspects of the present subject matter locally stimulate efferent nerves for the heart in an effort to stimulate a desired response while reducing the undesired effects of indiscriminate stimulation of the nervous system. Some embodiments of the present subject matter involve stimulating nerves which innervate the heart, e.g., the vagus nerve or nerve endings in the fat pads of the heart, and some embodiments of the present subject matter involve stimulating an efferent nerve trunk, such as the carotid sinus or aortic arch nerve. Neural stimulation (e.g., vagal nerve stimulation) can modulate cardiac contractility, and inhibit the local inflammatory response, likely creating a more favorable environment for exogenous cell transplantation (Lewis et al., *J. Physiol.*, 534:547 (2001); Tracey et al., *Nature*, 420:853 (2002); Lathrop and Spooner, *J. Cardiovasc. Electrophysiol.*, 12:841 (2001)), and/or enhancing the effect of other cardiac therapies including cardiac repair therapies, e.g., gene therapy, and/or cytokine therapy, and/or drug therapy, or endogenous stem cell localization to a cardiac region in need of repair. A "cytokine" is a relatively low molecular weight protein secreted by cells, e.g., cells of the immune system, for the purpose of altering the function(s) of those cells and/or adjacent cells. Cytokines include interleukins, e.g., molecules which regulate the inflammatory and immune response, as well as growth and colony stimulating factors. By "growth factor" is meant an agent that, at least, promotes cell growth or induces phenotypic changes. As used herein, a "drug" is an agent that is not a cytokine and optionally is not naturally produced by a cell or tissue, and which, in an effective amount, has a prophylactic or therapeutic effect. In one embodiment, a drug useful in the methods of the invention includes but is not limited to an anti-hypertensive agent, anti-arrhythmic agent, e.g., class III and IV antiarrhythmics, pressor, vasopressor, vasodilator, anti-hyperlipidemic agent, anti-anginal agent, ionotropic agent, diuretic, volume expander, thrombolytic, anti-platelet agent, beta-blocker, alpha-blocker, angiotensin converting enzyme (ACE) inhibitor, angiotensin receptor blocker, or any combination thereof.

Some embodiments of the invention stimulate efferent nerve trunks using a cuff electrode, and some embodiments stimulate efferent nerve trunks using an intravascular lead, e.g., a RV lead, positioned in a blood vessel proximate to the nerve, such that the electrical stimulation passes through the vessel wall to stimulate the efferent nerve trunk. Cuffs may be placed around efferent nerve trunks, such as the vagal nerve, to stimulate the cholinergic response. According to various embodiments of the present subject matter, efferent nerve trunks can be stimulated using a cuff or intravascularly-fed lead positioned in a blood vessel proximate to the efferent nerves.

Figure 2A:
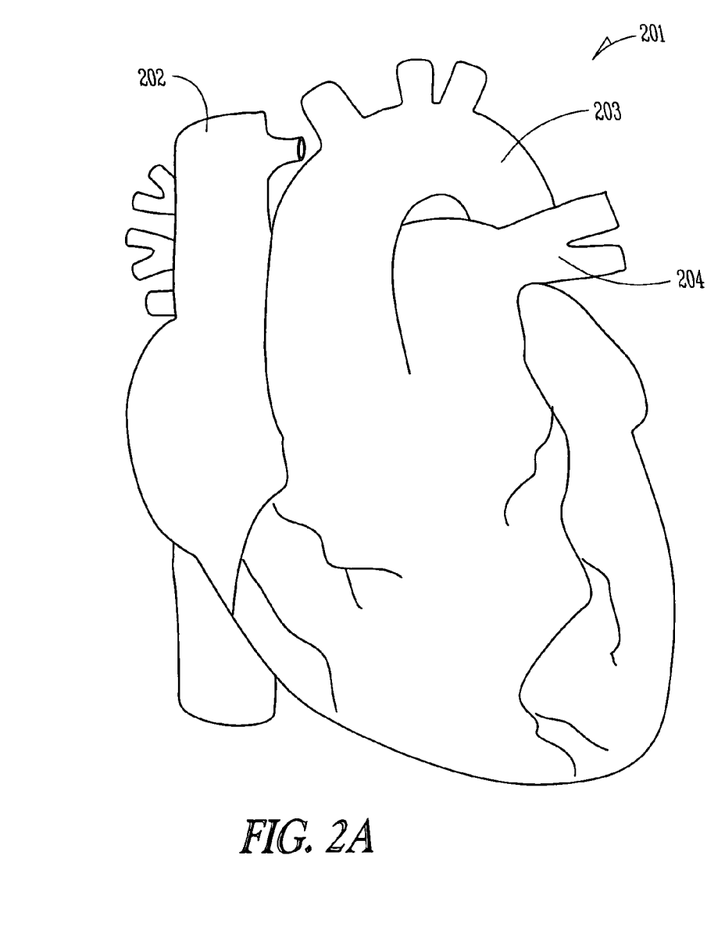
FIGS. 2A-2C illustrate a heart.
Figure 2B:
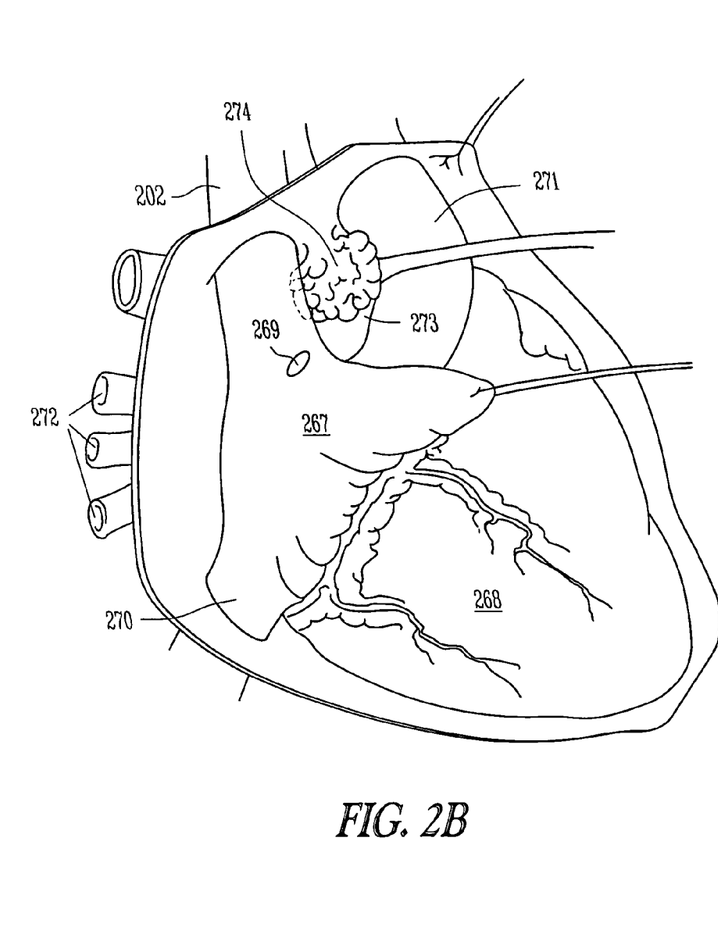
Figure 2C:
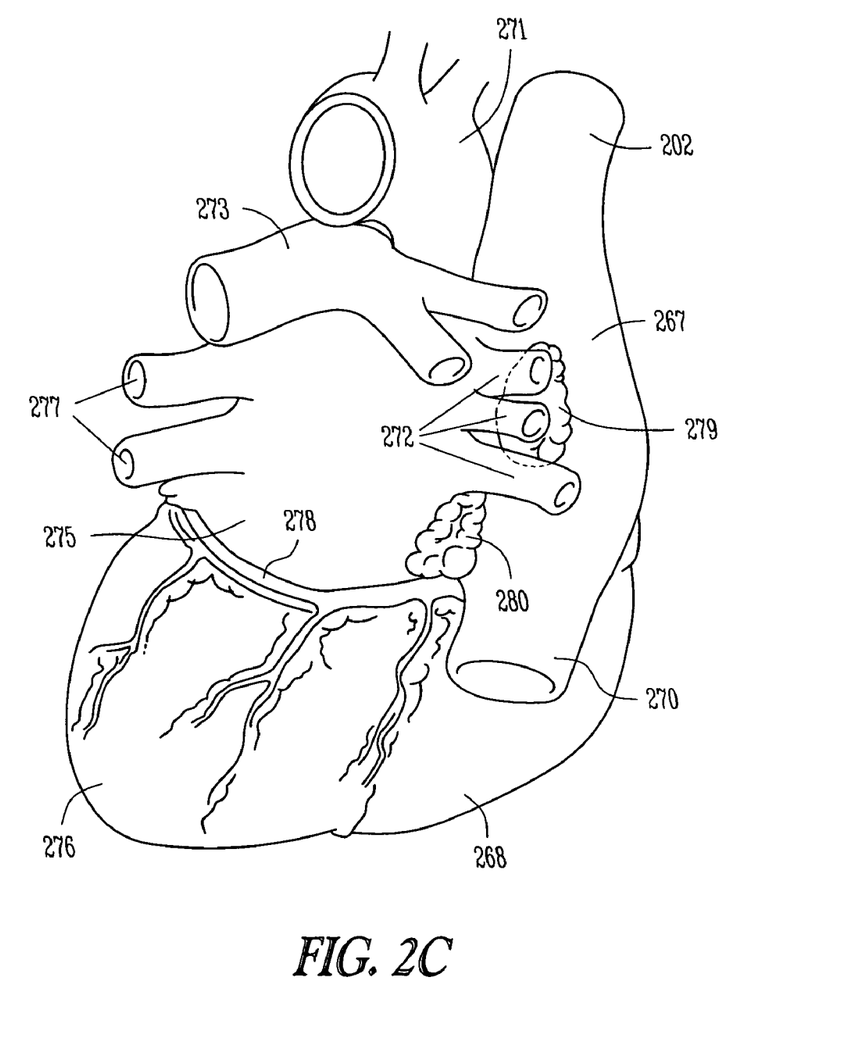

FIGS. 2A-2C illustrate a heart. As illustrated in FIG. 2A, the heart 201 includes a superior vena cava 202, an aortic arch 203, and a pulmonary artery 204. A lead is capable of being intravascularly inserted through a peripheral vein and through into the right atrium (RA) and/or right ventricle (RV) of the heart and/or a vessel near by, e.g., the pulmonary artery, superior vena cava, inferior vena cava, coronary sinus, left coronary veins, or internal jugular vein. Various embodiments stimulate efferent nerves which innervate the heart using a lead intravascularly positioned in vessels near the RV of the heart. In another embodiment, a neural cuff is positioned on an efferent parasympathetic nerve which innervates cardiac tissue. In other embodiments, an intravascular lead is placed near one or more cardiac fat pads, while in other embodiments, the lead is an epicardial lead, e.g., near or attached to a cardiac fat pad or RV. Thus, according to one aspect of the present subject matter, the nerve is stimulated by at least one electrode intravascularly inserted into a vessel near the heart. Alternatively, a wireless stimulating device may be positioned via catheter into a vessel near the heart. Control of stimulation and/or energy for stimulation may be supplied by another implantable or external device via ultrasonic or electromagnetic energy, or a combination thereof. Aspects of the present subject matter provide a relatively noninvasive surgical technique to implant a neural stimulator intravascularly, however, the invention is not limited to such techniques.

FIGS. 2B-2C illustrate the right side and left side of the heart, respectively, and further illustrate cardiac fat pads which have nerve endings. FIG. 2B illustrates the right atrium 267, right ventricle 268, sinoatrial node 269, superior vena cava 202, inferior vena cava 270, aorta 271, right pulmonary veins 272, and right pulmonary artery 273. FIG. 2B also illustrates a cardiac fat pad 274 between the superior vena cava and aorta. Nerve endings in the cardiac fat pad 274 are stimulated in some embodiments using an electrode screwed into the fat pad, and are stimulated in some embodiments using an intravenously-fed lead proximately positioned to the fat pad in a nearby vessel. FIG. 2C illustrates the left atrium 275, left ventricle 276, right atrium 267, right ventricle 268, superior vena cava 202, inferior vena cava 270, aorta 271, right pulmonary veins 272, left pulmonary vein 277, right pulmonary artery 273, and coronary sinus 278. FIG. 2C also illustrates a cardiac fat pad 279 located proximate to the right cardiac veins and a cardiac fat pad 280 located proximate to the inferior vena cava and left atrium. Nerve endings in the fat pad 279 are stimulated in some embodiments using an electrode screwed into the fat pad 279, and are stimulated in some embodiments using an intravenously-fed lead proximately positioned to the fat pad in a vessel. Nerve ending in the fat pad 280 are stimulated in some embodiments using an electrode screwed into the fat pad, and are stimulated in some embodiments using an intravenously-fed lead proximately positioned to the fat pad in a vessel.

Neural Stimulator Systems

Various embodiments of the present subject matter relate to neural stimulator (NS) devices or components. Various embodiments of the present subject matter include stand-alone implantable neural stimulator systems, include implantable devices that have integrated NS and cardiac rhythm management (CRM) components, and include systems with at least one implantable NS device and an implantable CRM device capable of communicating with each other either wirelessly or through a wire lead connecting the implantable devices. Integrating NS and CRM functions that are either performed in the same or separate devices improves aspects of the NS therapy and cardiac therapy by allowing these therapies to work together.

Various embodiments relate to a system that seeks to deliver electrically mediated NS therapy to patients. Various embodiments combine a "stand-alone" pulse generator with a minimally invasive, unipolar lead that directly stimulates nerves in the vicinity of the heart. This embodiment is such that general medical practitioners lacking the skills of specialist can implant it. Various embodiments incorporate a simple implanted system that can sense parameters indicative of blood pressure. This system adjusts the therapeutic output (waveform amplitude, frequency, duty cycle, etc.). In various embodiments, an implanted system includes a pulse generating device and lead system, the stimulating electrode of which is positioned near endocardial tissues using transvenous implant technique(s). Another embodiment includes a system that combines NS therapy with traditional bradyarrhythmia, tachyarrhythmia, and/or congestive heart failure (CHF) therapies. In another embodiment, a traditional CRM lead is modified to incorporate proximal electrodes that are naturally positioned near efferent nerves which innervate the heart or one or more cardiac fat pads. With these leads, distal electrodes provide CRM therapy and proximate electrodes stimulate efferent nerves which innervate the heart or one or more cardiac fat pads.

According to various embodiments, the lead(s) and the electrode(s) on the leads are physically arranged with respect to the heart in a fashion that enables the electrodes to properly transmit pulses and sense signals from the heart, and to stimulate the efferent nerves which innervate the heart, e.g., innervate one or more cardiac fat pads. As there may be a number of leads and a number of electrodes per lead, the configuration can be programmed to use a particular electrode or electrodes. According to various embodiments, one or more efferent nerve trunks are stimulated.

According to various embodiments, for example, the NS device is equipped with a telemetry coil, allowing data to be exchanged between it and the CRM device, allowing the NS device to modify therapy based on electrophysiological parameters such as heart rate, minute ventilation, atrial activation, ventricular activation, and cardiac events. In addition, the CRM device modifies therapy based on data received from the NS device, such as mean arterial pressure, systolic and diastolic pressure, and stimulation rate.

Some NS device embodiments are able to be implanted in patients with existing CRM devices, such that the functionality of the NS device is enhanced by receiving physiological data that is acquired by the CRM device. The functionality of two or more implanted devices is enhanced by providing communication capabilities between or among the implanted devices. In various embodiments, the functionality is further enhanced by designing the devices to wirelessly communicate with each other.

Programmed Therapy Applications

NS and/or CRM functions of a system, whether implemented in two separate and distinct implantable devices or integrated as components into one implantable device, includes processes for performing NS and/or CRM therapy or portions of the therapy. These processes can be performed by a processor executing computer-readable instructions embedded in memory, for example. These therapies include a number of applications, which have various processes and functions, some of which are identified and discussed below.

The processes and functions of these therapies are not necessarily mutually exclusive, as some embodiments of the present subject matter include combinations of two or more of the below-identified processes and functions.

A refractory period includes both absolute and relative refractory periods. Cardiac tissue is not capable of being stimulated during the absolute refractory period. The required stimulation threshold during an absolute refractory period is basically infinite. The relative refractory period occurs after the absolute refractory period. During the relative refractory period, as the cardiac tissue begins to repolarize, the stimulation threshold is initially very high and drops to a normal stimulation threshold by the end of the relative refractory period. Thus, according to various embodiments, a neural stimulator applies neural stimulation during either the absolute refractory period or during a portion of the relative refractory period corresponding a sufficiently high stimulation threshold to prevent the neural stimulation from capturing cardiac tissue.

The stimulation can be applied to an efferent nerve trunk such as the vagal nerve using a cuff electrode or an intravascularly-fed lead positioned proximate to the nerve trunk. The stimulation can be applied to cardiac fat pads using intravenously-fed leads or by screwing electrodes into the fat pads. The stimulation can be applied to efferent nerves such as the vagus nerve via a cuff or intravenously-fed lead. Modulation of Neural Stimulation Based on Cardiac Activity The present subject matter describes a method of modulating electrical stimulation of an efferent nerve based on cardiac activity, such as can be determined by the heart rate, minute ventilation, acceleration, pressure sensor, and combinations thereof, and/or the timing of cell therapy, gene therapy and/or cytokine or other drug therapy.

Indices of cardiac activity may be used to automatically modulate the electrical stimulation of efferent nerves which innervate the heart, allowing an implantable device to respond to changes in metabolic demand. According to various embodiments, a CRM device, such as a pacemaker, AICD or CRT devices, also has a neural stimulation lead. The device monitors cardiac activity through existing methods using, for example, a blended sensor. A blended sensor includes two sensors to measure parameters such as acceleration and minute ventilation. The output of the blended sensor represents a composite parameter. Various NS therapies use composite parameters derived from two or more sensed parameters as discussed within this disclosure. A pressure transducer can be used to determine activity. Furthermore, activity can be sensed using sensors that are or have been used to drive rate adaptive pacing. Examples of such sensors include sensor to detect body movement, heart rate, QT interval, respiration rate, transthoracic impedance, tidal volume, minute ventilation, body posture, electroencephalogram (EEG), electrocardiogram (ECG), electrooculogram (EOG), electromyogram (EMG), muscle tone, body temperature, pulse oximetry, time of day and pre-ejection interval from intracardiac impedance.

Various embodiments of the cardiac activity monitor includes a sensor to detect at least one pressure parameter such as a mean arterial parameter, a pulse pressure determined by the difference between the systolic and diastolic pressures, end systolic pressure (pressure at the end of the systole), and end diastolic pressure (pressure at the end of the diastole). Various embodiments of the cardiac activity monitor include a stroke volume monitor. Heart rate and pressure can be used to derive stroke volume. Various embodiments of the cardiac activity monitor use at least one electrogram measurement to determine cardiac activity. Examples of such electrogram measurements include the R—R interval, the P—R interval, and the QT interval. Various embodiments of the cardiac activity monitor use at least one electrocardiogram (ECG) measurement to determine cardiac activity. Neural Stimulation and Cell, Gene, Cytokine and/or Drug Therapy To Treat Impaired Myocardial Function Following a myocardial infarction, myocytes in the infarcted region die and are replaced by scar tissue, which has different mechanical and elastic properties from functional myocardium. Over time, this infarcted area can thin and expand, causing a redistribution of myocardial stresses over the entire heart. Eventually, this process leads to impaired mechanical function in the highly stressed regions and heart failure. The highly stressed regions are referred to as being heavily "loaded" and a reduction in stress is termed "unloading."

In one aspect of the present invention, an implantable NS device modulates cardiac activity before, during, after, or any combination thereof, cell therapy, gene therapy, and/or cytokine or other drug therapy. In another aspect of the present subject matter relates to an implantable device that monitors and/or modulates cardiac electrical activity before, during, after, or any combination thereof, cell therapy, gene therapy, and/or cytokine therapy. An implantable device (for example, a CRM device with a NS lead) may monitor cardiac electrical activity. Upon detection of an undesirable cardiac activity, and/or before, during and/or after cell, gene and/or cytokine therapy, the device stimulates the efferent nerve and/or cardiac fat pads. In various embodiments, efferent nerves are stimulated directly with a cuff electrode, or with a lead intravenously placed near the efferent nerve. For instance, efferent nerves such as the vagus nerve are stimulated directly with a cuff electrode, or with a lead intravenously placed near the efferent nerve. In various embodiments, a cardiac fat pad is stimulated using an electrode screwed into the fat pad, or a lead intravenously fed into a vessel or chamber proximate to the fat pad.

According to various embodiments, systemic blood pressure, heart rate or cardiac output, or a surrogate parameter, are monitored during stimulation to insure that an appropriate level of stimulation is delivered.

For instance, a patient with impaired cardiac function due to a myocardial infarction is subjected to cell therapy, e.g., exogenous cells including bone marrow derived cells, skeletal myoblasts, or stem cells such as hematepeetie hematopoietic, SP, or neural stem cells, or exogenous agent treatment, e.g., the administration of a cytokine which enhances stem cell homing and/or proliferation (such as G-CSF, SDF, e.g., SDF1, HGF, IGF, and the like) or a gene therapy vector, e.g., one which encodes a cytokine and/or stem cell homing and/or proliferation factor. In conjunction, the patient would receive a NS device, or a CRM device that contains a neural stimulation lead. In various embodiments, the neural stimulation lead is intravascularly placed proximal to the appropriate neural stimulation site. Intermittent neural stimulation (e.g., 5 to 10second bursts per minute at a frequency of 20 to 120 Hz) would be provided for a redetermined period of time. Alternatively, the duration of neural stimulation would be determined by a physiological sensor of cardiac function. The neural stimulation would, in this way, create a more favorable environment for the localization, proliferation and/or differentiation of implanted donor cells or endogenous stem cells at or near the site of infarction, enhance the transfer and/or expression of gene therapy vectors to the cells of a patients, and/or enhance the effects of cytokine therapy.

Neural stimulation can be used to unload after cell, gene and/or cytokine therapy. For example, a stimulation lead can be implanted after a myocardial infarction. In various embodiments, the stimulation lead is implanted near the left ventricle. Various embodiments implant stimulation cuffs or leads to stimulate efferent nerves, and implant electrode screws or leads to stimulate cardiac fat pads. Moreover, electrical pre-excitation of a heavily loaded region will reduce loading on this region. This pre-excitation may significantly reduce cardiac output resulting in sympathetic activation and an increase in global stress, ultimately leading to deleterious remodeling of the heart. This process may be circumvented by increased neural stimulation to reduce the impact of this reflex. Thus, activation of the parasympathetic nervous system during pre-excitation may prevent the undesirable side-effects of unloading by electrical pre-excitation.

One of ordinary skill in the art will understand that, the modules and other circuitry shown and described herein can be implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. For example, various embodiments combine two or more of the illustrated processes. Two or more sensed parameters can be combined into a composite parameter used to provide a desired neural stimulation (NS) therapy. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Sources of Donor Cells for Cell-Based Therapies

Sources for donor cells in cell-based therapies for cardiac repair include skeletal muscle derived cells, for instance, skeletal muscle cells and skeletal myoblasts; cardiac derived cells, myocytes, e.g., ventricular myocytes, atrial myocytes, SA nodal myocytes, AV nodal myocytes, and Purkinje cells; bone marrow-derived cells, e.g., mesenchymal cells and stromal cells; smooth muscle cells; fibroblasts; SP cells; or pluripotent cells or totipotent cells, e.g., teratoma cells, hematopoietic stem cells, for instance, cells from cord blood and isolated CD34$^+$ cells, multipotent adult progenitor cells, adult stem cells and embryonic stem cells. In one embodiment, the donor cells are autologous cells, however, non-autologous cells, e.g., allogeneic or xenogeneic cells, may be employed. The donor cells can be expanded in vitro to provide an expanded population of donor cells for administration to a recipient animal. In addition, donor cells may be treated in vitro as exemplified below. Sources of donor cells and methods of culturing those cells are known to the art. See, for example, U.S. Pat. No. 5,130,141 and Jain et al., (Circulation, 103, 1920 (2001)), wherein the isolation and expansion of myoblasts from skeletal leg muscle is discussed (see also Suzuki et al., Circulation 104 1-207 (2001), Douz et al., Circulation, 111-210 (2000) and Zimmerman et al., Circulation Res 90, 223 (2002)). Published U.S. application 20020110910 discusses the isolation of and media for long term survival of cardiomyocytes. U.S. Pat. No. 5,580,779 discusses isolating myocardial cells from human atria and ventricles and inducing the proliferation of those myocardial cells. U.S. Pat. No. 5,103,821 discusses isolating and culturing SA node cells. For SA node cells, the cells may be co-cultured with stem cells or other undifferentiated cells. U.S. Pat. No. 5,543,318 discusses isolating and culturing human atrial myocytes. U.S. Pat. Nos. 6,090,622 and 6,245,566 discusses preparation of embryonic stem cells, while U.S. Pat. No. 5,486,359 discusses preparation of mesenchymal cells.

The donor cells may also be manipulated in vitro to introduce one or more desirable genes (transgenes) to the cells. Preferably, the genetically modified (transgenic) donor cells include a transgene that enhances cellular proliferation, cellular localization, cellular survival, cellular differentiation and/or cellular function of the donor cells in the recipient, optionally by secreting a gene product encoded by the transgene. In one embodiment the expression of the transgene is controlled by a regulatable or tissue-specific transcription regulatory control element such as an enhancer or promoter, e.g., a promoter sensitive to signals delivered by a device such as an implantable device (see, for instance, U.S. patent application Ser. No. 10/788,906 filed on Feb. 27, 2004, entitled "METHOD AND APPARATUS FOR DEVICE CONTROLLED GENE EXPRESSION,"the disclosure of which is incorporated by reference herein), or a cardiac myocyte-specific promoter. The transgene may be introduced to donor cells by any means including but not limited to liposomes, electroporation, naked DNA, or viral-mediated transduction, for instance, via adenovirus, adeno-associated virus, retrovirus or lentivirus vectors.

Donor cells may also be treated in vitro by subjecting them to mechanical, electrical, biological conditioning, conditioning associated with altered physical conditions, e.g., hypoxic conditions, or any combination thereof. The conditioning may include continuous or intermittent exposure to the exogenous stimuli. Preferred exogenous agents include those which enhance the survival, localization, differentiation, proliferation and/or function of donor cells after transplant.

A. Mechanical Conditioning

Mechanical conditioning includes subjecting donor cells to a mechanical stress that simulates the mechanical forces applied upon cardiac muscle cells in the myocardium due to the cyclical changes in heart volume and blood pressure. In one embodiment, a cyclic mechanical stress is applied to the donor cells. In one embodiment, the cyclical mechanical stress applied to donor cells results in the cyclical deformation of these cells, resembling the cyclical deformation (contraction) of cardiac muscle cells in vivo. The mechanical stress includes subjecting one or more donor cells, preferably a population of donor cells, to a mechanical force in one dimension and in one direction, or alternatively, in one dimension and in two or more opposite directions, for example, causing the donor cells to stretch and relax at a predetermined frequency for a predetermined duration. Mechanical conditioning can result in donor cells that are capable of contracting upon excitation by action potentials.

Mechanical conditioning preferably alters gene expression, protein synthesis, and/or the activity of one or more cellular kinases in donor cells, and in one embodiment results in proliferation and/or differentiation of the donor cells. In one embodiment, mechanical conditioning of donor cells results in an altered expression profile, e.g., an altered expression profile for genes encoding BMP, VEGF, angiotensin II, and the like, in the donor cells. In one embodiment, mechanical conditioning of donor cells results in an increase in the number and/or activity of contractile elements including actin and myosin filaments, which are protein structures that interact with each other during muscle contraction. Donor cells subjected to mechanical conditioning thus develop contractility that is characteristic of muscle cells.

In one embodiment, the mechanical conditioning includes subjecting donor cells to a mechanical force so that the donor cells are physically extended in at least one direction by approximately 5% to 20% of their length, and at a frequency of 0.25 to 2 Hz. In other words, at least one donor cell is forced to increase its length by 5% to 20% at 0.25 to 2 times per second. This simulates the mechanical tension which cardiac muscle cells are subject to under physiological conditions in vivo. In one embodiment, donor cells are plated on a controllably deformable culturing substrate in the presence of culturing media. The substrate is cyclically deformed to simulate the mechanical displacement of cardiac muscle. In one specific embodiment, the substrate includes a distensible strip made of medical grade silicone. Donor cells are plated on the distensible strip. The distensible strip is stretched and released, such that the donor cells on it change their length with the distensible strip in a manner simulating the cardiac muscle cells in vivo. One example of such an apparatus for applying mechanical stress to cells in a culture is given in Terracio et al., *In Vitro Cellular & Developmental Biology*, 24(1), 53-58, 1988, where the silicone strip is subject to calibrated mechanical tension created with a variable speed motor.

In one embodiment, the mechanical conditioning is applied continuously for a predetermined period of time. In one specific embodiment, the predetermined period is in the range of 1 to 14 days. In another embodiment, the mechanical conditioning is applied intermittently for a predetermined period of time interrupted by one or more resting (non-stimulating) periods. In one specific embodiment, the mechanical conditioning is applied with a duty cycle that is in the range of 5% to 75% for a predetermined period that is in the range of 1 to 14 days.

B. Electrical Conditioning

Electrical conditioning includes subjecting donor cells to electrical conditions that simulate the electrical conditions in the myocardium which result in contraction of the heart. In the heart, contraction results primarily from the contractions of atrial and ventricular muscle fibers. Contraction of atrial and ventricular muscle fibers is slower and is of a longer duration than the contraction of skeletal muscle. Cardiac muscle and skeletal muscle, however, share a number of common anatomic characteristics. In the same manner as skeletal muscle, cardiac muscle is made up of elongated fibers with transverse dark and light bands. The dark bands correspond to the boundaries between cells. Each fiber is made up of individual cells connected in series with each other. Cardiac muscle includes myofibrils, which are the longitudinal parallel contractile elements composed of actin and myosin filaments that are almost identical to those of the skeletal muscle. The actin and myosin filaments interdigitate and slide along each other during contraction. Contraction is caused by action potentials that propagate along or spread over the muscle fibers. The propagation of action potentials results from changes in the electrical potential across muscle cell membranes, referred to as membrane potential. The changes in the membrane potential are in turn caused by flow of sodium, potassium, and/or calcium ions across the muscle cell membranes through ion channels, which are formed by protein molecules in the cell membranes. Some types of muscle include protein structures called gap junctions through which ions flow from one muscle cell to another. Gap junctions allow the flow of ions, and hence the propagation of action potentials, directly from one cell to another. Cardiac muscle has at least two unique anatomic characteristics: a high density of calcium-sodium channels and a high density of gap junctions. These characteristics distinguish cardiac muscle from skeletal and other types of muscle.

Action potential propagates in skeletal muscle mainly via the sudden opening of fast sodium channels that allow sodium ions to enter the muscle cells. Each opening of a fast sodium channel lasts for only a few ten-thousandths of a second. In contrast, cardiac muscle includes both fast sodium channels and slow calcium-sodium channels that allow both calcium and sodium to enter the muscle cells. Each opening of a slow calcium-sodium channel lasts for several tenths of a second. This results in the long duration of contraction, which characterizes cardiac muscle.

Gap junctions in cardiac muscle fibers allow relatively free flow of ions across the cell membranes along the fiber axes. Thus, action potentials travel from one cell to another with little resistance. Cardiac muscle is a syncytium (mass of fused cells) with muscle fibers arranged in a latticework in which the fibers branch, merge, and branch again. When one cell in the syncytium becomes excited, the action potential propagates from cell to cell and spreads throughout the latticework interconnections. The heart includes two syncytiums, the atrial syncytium and the ventricular syncytium. In a normal heart, action potentials are conducted from the atrial syncytium to the ventricular syncytium through a conduction system, the A-V bundle, and the atrial syncytium contracts before the ventricular syncytium.

In one embodiment, electrical conditioning includes providing electrical stimuli such as cardiac pacing pulses to the donor cells in culture so as to cause them to contract. In another embodiment, the electrical conditioning includes providing a static electrical field to the donor cells in culture. Electrical conditioning can result in the donor cells proliferating and differentiating into cardiac muscle cells or cells having substantially similar functions as cardiac muscle cells.

In one embodiment, electrical conditioning of donor cells results in cells with one or more characteristics of cardiac muscle cells, including a high density of calcium-sodium channels and a high density of gap junctions. Such electrical conditioning may occur in vitro and/or in vivo. Moreover, once the donor cells are implanted in the myocardium, they are subject to the pattern of contractions in the myocardium and may, if they are not cardiac muscle cells, differentiate into cardiac muscle cells. In one embodiment, the donor cells are electrically conditioned prior to implantation into the myocardium. In one embodiment, the electrical conditioning includes subjecting the donor cells to an artificially induced contraction pattern that simulates the physiological contractions of cardiac muscle cells in vivo. The contraction pattern is induced by electrical stimulation such as by cardiac pacing. In a further embodiment, the donor cells are also subjected to an electrical field stimulation that simulates the environment in the myocardium. Electrical conditioning of donor cells, including cardiac pacing and/or field stimulation, may result in an altered expression profile of the donor cells, including increased calcium-sodium channel expression and/or increased expression and/or formation of gap junctions. For instance, electrical conditioning may increase angiotensin II or VEGF expression, which in turn increases gap junction formation.

In one embodiment, pacing pulses are generated by a pacemaker or any pulse generator capable of producing the pacing pulses. The donor cells are placed in a culturing media including fluids which simulate the extracellular fluid of the myocardium. The pacing pulses are delivered to the donor cells through two electrodes placed in the culture. Parameters controlling the delivery of the cardiac pacing pulses include pacing rate, pacing voltage, and pacing pulse width, which are each selected from a physiological range to simulate the electrical activities within the myocardium. In one specific embodiment, the pacing rate is in the range of 15 to 120 beats per minute; the pacing voltage is in the range of 0.1 to 10 volts; and the pacing pulse width is in the range of 0.1 to 10 milliseconds. In one embodiment, cardiac pacing is applied to the donor cells continuously for a predetermined period of time. In one specific embodiment, the predetermined period of time is in the range of 1 to 14 days. In another embodiment, cardiac pacing is applied intermittently to the donor cells for a predetermined period that is interrupted by one or more resting (non-pacing) periods. In one specific embodiment, cardiac pacing is applied to the donor cells with a duty cycle in the range of 5% to 75% for a predetermined period that is in the range of 1 to 14 days.

In one embodiment, a static electrical field is applied to a donor cell culture. In one specific embodiment, the field strength is in the range of 1 to 100 volts per meter. In one embodiment, the electrical field is applied continuously for a predetermined period. In one specific embodiment, the predetermined period is in the range of 1 to 14 days. In another embodiment, the electrical field is applied for a predetermined period that is interrupted by one or more resting (non-stimulation) periods. In one specific embodiment, the electrical field is applied with a duty cycle of 5% to 75% for a predetermined period that is in the range of 1 to 14 days.

C. Biological Conditioning Biological conditioning includes subjecting donor cells to exogenous agents, e.g., differentiation factors, growth factors, angiogenic proteins, survival factors, and cytokines, as well as to expression cassettes including transgenes encoding a gene product including, but not limited to, an angiogenic protein, a growth factor, a differentiation factor, a survival factor, a cytokine, a cardiac cell-specific structural gene product, a cardiac cell-specific transcription factor, or a membrane protein, e.g., a gap junction protein, or comprising an antisense sequence, for instance, a ribozyme, or any combination thereof. The expression cassette optionally includes at least one control element such as a promoter, optionally a regulatable promoter, e.g., one which is inducible or repressible, an enhancer, or a transcription termination sequence. Preferably, the promoter and/or enhancer is one which is cell- or tissue-specific, e.g., cardiac cell-specific, or a promoter sensitive to signals delivered by a device such as an implantable device (see, for instance, U.S. pat. application Ser. No. 10/788,906 filed on Feb. 27, 2004, entitled "METHOD AND APPARATUS FOR DEVICE CONTROLLED GENE EXPRESSION"). For instance, the enhancer may be a muscle creatine kinase (mck) enhancer, and the promoter may be an alpha-myosin heavy chain (MyHC) or beta- MyHC promoter (see Palermo et al., Circ. Res 78 504 (1996)).

Transgenes

In one embodiment, the transgene (a polynucleotide) encodes a gene product including but not limited to an angiogenic protein, e.g., a fibroblast growth factor (FGF) such as acidic - FGF, basic-FGF, FGF-3, FGF-4, FGF-5, FGF-6, FGF-7, FGF-8 and FGF -9, vascular endothelial growth factor (VEGF), e.g., VEGF-A, VEGF-B, VEGF-C, VEGF-D, VEGF-E, VEGF-F, $VEGF_{145}$, $VEGF_{121}$, $VEGF_{120}$, $VEGF_{164}$, $VEGF_{165}$, $VEGF_{189}$, and $VEGF_{206}$, IGF-1, TGF-beta, e.g., TGF-beta$_1$, leukemia inhibitory factor (LIF) alone or in combination with other cytokines, a myogenic factor, e.g., myoD, RyRZ (cardiac ryanodine receptor), Del I, myogenin, parvalbumin, Myf5, and MRF, transcription factors (GATA such as GATA-4and dHAND/eHAiND), cytokines such as cardiotrophin-1, calsequestrin, neuregulin, for instance, neuregulin 1, 2or 3, hepatocyte growth factor (HGF), insulin-like growth factor (IGF), e.g., IGF 1, granulocyte colony stimulating factor (G-CSF) and stromal cell derived factor (SDF), homeobox gene products, e.g., Csx, tinman, and the NKx family, e.g., NKx 2.5, transferrin, platelet-derived growth factor (PDGF), epidermal growth factor (EGF), adrenocorticotrophin, macrophage colony-stimulating factor, protein kinase C activators, endothelial growth factor, mutant G protein receptor kinase (GRK), adenylyl cylase (AC), e.g., cardiac AC such as human type II, V or VI adenyl cylase (U.S. Pat. No. 6,436,672), V2 vasopressin receptor, sarcoplasmic reticulum Ca2$^+$ATPase (SERCA2a), phospholamban N-cadherin, connexin-40, connexin-41, connexin-42, connexin-43, or connexin-45, contractable proteins, e.g., myosin heavy chain (MyHC), myosin light chain (MyLC), myosin binding protein C, actin, tropomyosin, troponin, e.g., troponin T, M protein, tropomodulin, myofibrillar protein, stress related protein, e.g., heat shock protein (HSP) such as HSP70i, HSP27, HSP40 or HSP60,α-1antitrypsin, HF-1a , HF-1b , MEF2, BMP-2, BMP-4, BMP-7, BMP -17, BMP-18, Pax7, oxytocin, oxytocin receptor, myocyte nuclear factor, Frzb (see published US application 20020147329), Rb-interacting zinc finger protein (U.S. Pat. No. 6,468,985), eNOS, iNOS, serine/threonine protein phosphatase, cardiac hypertrophy factor, CT-1, α,β,γ or δsarcoglycan, hypoxia inducible factor 1α, bcl-2, FasL, cytokine gp 130receptor, gp130, adenosine A3receptor, angiogenin, e.g., angiogenin-1 or angiogenin-2, TNFα, dystrophin, tafazzin, desmin, lamin, troponin C, caspase inhibitors, ERK-type of MAP kinases (p42 and p44, anti -apoptosis), IL-1B, serum releasing factor, and ILGF (I and II), NGF, growth hormone, e.g., human growth hormone, angiotensin, e.g., angiotensin II, hepatocyte growth factor (HGF), ARK$_{Ct}$, endothelial GF121, angiotensin type II receptor, p16INK4a, sodium channel protein, e.g., SCN5A, Akt, C reactive protein, MiRPI, cardiac endothelin-1, KCNEI (I$_{Ks}$), protein kinase C, HIF - 1α, p38MAPK, Cox-2, phospholamban, matrix metalloproteinases, adrenergic receptors (AR) and kinases therefore, e.g., betaAR and betaARK, cytochrome oxidase B subunit III, ATP synthase subunit 6, calcium channel proteins such as voltage gated Ca$^{2+}$ channels, potassium channel proteins such as KCNA5(Kv1.5), KCND2(Kv4.2), KCND3(Kv 4.3, I$_{to}$), KCNEI (minK), KCNE2, KCNQ 1, as well as K+ inwardly rectifying channels such as Kir3.1(KCNJ3), KCNH2(HERG, I$_{kr}$), Kv4.3, Kir3.4, Kir6.1and Kir6.2, the sodium-calcium exchanger (I$_{Na/Ca}$), e.g., NCKX1-4, HCN, Kir2.1, Kir3.1/3.4, ERG, KvLQT1, Kv4.2/4.3, Kv1.4, KCh1P2, Kv1.5/3.1, Ca$_v$1.2, Ca$_v$1.3, Ca$_v$3.1, Ca$_v$3.3, Na$_v$1.5, platelet-derived endothelial-cell growth factor (PD-ECGF), transforming growth factor-a (TGF-α), transforming growth factor - β (TGF-β), thrombospondin (TSP), proliferin, ephrin-A1(B61), e-selectin, chicken chemotactic and angiogenic factor (cCAF), leptin, heparin affin regulatory peptide (HARP), platelet derived growth factor (PDGF), e.g., PDGF-AA, PDGF-AB or PDGF-BB, heparin, a complement of the polynucleotide encoding the gene product, or encodes an inhibitor of the gene product. gene product, or encodes an inhibitor of the gene product.

In another embodiment, e.g., for cells from a mammal with an inherited or acquired disorder such as one characterized by overexpression of certain endogenous genes, the transgene may comprise antisense or ribozyme sequences which substantially correspond to the reverse complement of at least a portion of the endogenous gene, and which, when expressed in a host cell, results in a decrease in the expression of the endogenous gene. Alternatively, the transgene may comprise sequences which, after homologous recombination with the endogenous gene, result in a decrease in the expression of the endogenous gene. For instance, the use of antisense vectors resulting in the decreased expression of the following gene products may be beneficial in autologous cell therapy, gene products including, but not limited to, those which induce apoptosis, e.g., Fas, Bax1 and Apol, or a Na/Ca exchanger, or a mitogen-activated protein (MAP) kinase, Janus kinase (JAK)/signal transducer or activator of transcription, calcium/calmodulin-dependent protein phosphatase, calcineurin, carnitine palmoyl-transferase I, matrix metalloproteinase, eNOS, iNOS, serine/threonine protein phosphatase, or stress response mitogen activated protein kinase, e.g., Junk and p38MAPK.

For purposes of the present invention, control elements, such as muscle-specific and inducible promoters, enhancers and the like, will be of particular use. Such control elements include, but are not limited to, those derived from the actin and myosin gene families, such as from the myoD gene family (Weintraub et al., *Science*, 251, 761 (1991)); the myocyte-specific enhancer binding factor MEF-2 (Cserjesi and Olson, *Mol. Cell Biol.*, 11, 4854 (1991)); control elements derived from the human skeletal actin gene (Muscat et al., *Mol. Cell Bio.*, 7, 4089 (1987)) and the cardiac actin gene; muscle creatine kinase sequence elements (Johnson et al., *Mol. Cell Biol.*, 9, 3393 (1989)) and the murine creatine kinase enhancer (mCK) element; control elements derived from the skeletal fast-twitch troponin C gene, the slow-twitch cardiac troponin C gene and the slow-twitch troponin I gene; hypoxia-inducible nuclear factors (Semenza et al., *Proc. Natl. Acad. Sci. USA*, 88, 5680 (1991); Semenza et al., *J. Biol. Chem.*, 269, 23757); steroid-inducible elements and promoters, such as the glucocorticoid response element (GRE) (Mader and White, *Proc. Natl. Acad. Sci. USA*, 90, 5603 (1993)); the fusion consensus element for RU486 induction; and elements that provide for tetracycline regulated gene expression (Dhawan et al., *Somat. Cell. Mol. Genet.*, 21, 233 (1995); Shockett et al., *Proc. Natl. Acad. Sci. USA*, 92, 6522 (1995)).

Cardiac cell restricted promoters include but are not limited to promoters from the following genes: a α-myosin heavy chain gene, e.g., a ventricular α-myosin heavy chain gene, β-myosin heavy chain gene, e.g., a ventricular β-myosin heavy chain gene, myosin light chain 2v gene, e.g., a ventricular myosin light chain 2 gene, myosin light chain 2a gene, e.g., a ventricular myosin light chain 2 gene, cardiomyocyte -restricted cardiac ankyrin repeat protein (CARP) gene, cardiac α-actin gene, cardiac m2 muscarinic acetylcholine gene, ANP gene, BNP gene, cardiac troponin C gene, cardiac troponin I gene, cardiac troponin T gene, cardiac sarcoplasmic reticulum Ca-ATPase gene, skeletal α-actin gene, as well as an artificial cardiac cell-specific promoter.

Further, chamber-specific promoter promoters may also be employed, e.g., for atrial-specific expression, the quail slow myosin chain type 3 (MyHC3) or ANP promoter, may be employed. For ventricle-specific expression, the iroquois homeobox gene may be employed. Nevertheless, other promoters and/or enhancers which are not specific for cardiac cells or muscle cells, e.g., RSV promoter, may be employed in the expression cassettes and methods of the invention.

Other sources for promoters and/or enhancers are promoters and enhancers from the Csx/NKX 2.5 gene, titin gene, α-actinin gene, myomesin gene, M protein gene, cardiac troponin T gene, RyR2 gene, Cx40 gene, and Cx43 gene, as well as genes which bind Mef2, dHAND, GATA, CarG, E-box, Csx/NKX 2.5, or TGF-beta, or a combination thereof.

Preferably, the transgenic donor cells include a transgene that enhances the proliferation, engraftment, survival, differentiation and/or function of the donor cells. In one embodiment, the expression of the transgene is controlled by a regulatable or tissue-specific, e.g., cardiomyocyte-specific promoter. Optionally, a combination of vectors each with a different transgene can be employed.

Delivery of exogenous transgenes may be accomplished by any means, e.g., transfection with naked DNA, e.g., a vector comprising the transgene, liposomes, calcium-mediated transformation, electroporation, or transduction, e.g., using recombinant viruses. A number of transfection techniques are generally known in the art. See, e.g., Graham et al., *Virology*, 52, 456 (1973), Sambrook et al., *Molecular Cloning: A Laboratory Manual*, Cold Spring Harbor Laboratories, New York (1989), Davis et al., *Basic Methods in Molecular Biology*, Elsevier (1986) and Chu et al., *Gene*, 13, 197 (1981). Particularly suitable transfection methods include calcium phosphate co-precipitation (Graham et al., *Virol.*, 52, 456 (1973)), direct microinjection into cultured cells (Capecchi, *Cell*, 22, 479 (1980)), electroporation (Shigekawa et al., *BioTechniques*, 6, 742 (1988)), liposome-mediated gene transfer (Mannino et al., *BioTechniques*, 6, 682 (1988)), lipid-mediated transduction (Felgner et al., *Proc. Natl. Acad. Sci. USA*, 84, 7413 (1987)), and nucleic acid delivery using high-velocity microprojectiles (Klein et al., *Nature*, 327, 70 (1987)). Preferred recombinant viruses to deliver exogenous transgenes to cells include recombinant lentiviruses, retroviruses, adenoviruses, adeno-associated viruses (AAV), and herpes viruses including cytomegalovirus.

In one embodiment, recombinant AAV (rAAV) is employed to deliver a transgene to donor cells. Myoblasts are transduced either while actively dividing, or as a differentiated cell culture. Differentiation is induced by placing subconfluent myoblasts in DMEM containing 2% horse serum and standard concentrations of glutamine and penicillin-streptomycin for an interval of four days prior to transduction. Verification of differentiation is by microscopic analysis to determine the presence of multinucleated myotubes in culture. Myotubes (differentiated cells) or myoblasts (dividing cells) are transduced in culture.

Other Exogenous Agents

In another embodiment, the exogenous agent includes but is not limited to an angiogenic protein, e.g., a FGF such as acidic-FGF, basic-FGF, and FGF-5, VEGE, e.g., $VEGF_{145}$, $VEGF_{121}$, $VEGF_{120}$, $VEGF_{164}$, $VEGF_{165}$, $VEGF_{189}$, and $VEGF_{206}$, IGF-1, TGF-beta, e.g., TGF -$beta_1$, LIF alone or in combination with other cytokines, a myogenic factor, e.g., myoD, RyRZ (cardiac ryanodine receptor), Del I, myogenin, parvalbumin, Myf5, and MRF, GATA such as GATA-4and dHAND/eHAND), cytokines such as cardiotrophin-1, calsequestrin, neuregulin, for instance, neuregulin 1, 2 or 3, HGF, IGF, G-CSF and SDF, homeobox gene products, e.g., Csx, tinman, and the NKx family, e.g., NKx 2.5, transferrin, PDGF, EGF, adrenocorticotrophin, macrophage colony-stimulating factor, protein kinase C activators, endothelial growth factor, β2 adrenergic receptor (1or 2), mutant G protein receptor kinase (GRK), AC, e.g., cardiac AC such as human type II, V or VI adenyl cylase (U.S. Pat. No. 6,436, 672), V2vasopressin receptor, SERCA2a, phospholamban ,β-adrenergic receptor kinase, N-cadherin, connexin-40, connexin-42, connexin-43, MyHC, MyLC, myosin binding protein C, actin, tropomyosin, troponin, e.g., troponin T, M protein, tropomodulin, myofibrillar protein, stress related protein, e.g., HSP such as HSP70i, HSP27, HSP40 or HSP60, α1 antitrypsin, HF1-a, HF-1b, MEF2, HGF, BMP-2, BMP4, BMP-17, BMP-18, Pax7, oxytocin, oxytocin receptor, myocyte nuclear factor, Frzb (see published US application 20020147329), Rb-interacting zinc finger protein (U.S. Pat. No. 6,468,985), eNOS, iNOS, serine/threonine protein phosphatase, cardiac hypertrophy factor, CT-1, α,β,γ or δ sarcoglycan, hypoxia inducible factor 1α, bcl-2, FasL, cytokine gp 130 receptor, gp130, Akt, adenosine A3receptor, angiogenin, e.g., angiogenin-1or angiogenin-2, TNFα, dystrophin, tafazzin, desmin, lamin, troponin C, caspase inhibitors, ERK type of MAP kinases (p42and p44, anti-apoptosis), IL-1B, serum releasing factor, and ILGF (I and II), NGF, growth hormone, e.g., human growth hormone, angiotensin, e.g., angiotensin II, inotropes, norepinephrine, retinoic acid, preconditioned media, e.g., from ES cells which contains a plurality of growth factors, or other biological agents disclosed herein, or dexamethasone, 5azacytidine or other drug. Such agents may also be administered to a mammal prior to, during, or after cell therapy and/or gene therapy, or any combination thereof.

Compositions, Dosages and Routes of Administration

The amount of agent administered, including cells, gene therapy vectors and/or one or more cytokines which are exogenously administered, and including agents released from a device, in conjunction with electrical therapies described herein, will vary depending on various factors including, but not limited to, the agent chosen, the disease, whether prevention or treatment is to be achieved, and if the agent is modified for bioavailability and in vivo stability. Thus, the agents of the invention may be employed in conjunction with other therapies, e.g., therapies for ischemia or arrhythmias, including gene therapies and/or cell therapies, e.g., see U.S. Pat. application Ser. No. 10/723,258, filed on Nov. 25, 2003, entitled "METHOD AND APPARATUS FOR CELL AND ELECTRICAL THERAPY OF LIVING TISSUE" and U.S. Pat. application Ser. No. 10/788,906, filed on Feb. 27, 2004, entitled "METHOD AND APPARATUS FOR DEVICE CONTROLLED GENE EXPRESSION", the disclosures of which are incorporated herein by reference in their entirety.

The amount of agent administered, including cells, gene therapy vectors and/or one or more cytokines which are exogenously administered, and including agents released from a device, in conjunction with electrical therapies described herein, will vary depending on various factors including, but not limited to, the agent chosen, the disease, whether prevention or treatment is to be achieved, and if the agent is modified for bioavailability and in vivo stability. Thus, the agents of the invention may be employed in conjunction with other therapies, e.g., therapies for ischemia or arrhythmias, including gene therapies and/or cell therapies, e.g., see U.S. patent application Ser. No. 10/723,258, filed on Nov. 25, 2003, entitled "METHOD AND APPARATUS FOR CELL AND ELECTRICAL THERAPY OF LIVING CELLS" and U.S. patent application Ser. No. 10/788,906, filed on Feb. 27, 2004, entitled "METHOD AND APPRATUS FOR DEVICE CONTROLLED GENE EXPRESSION", the disclosures of which are incorporated herein by reference in their entirety.

Administration of the agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms comprising the agents of the invention, which, as discussed below, may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the agent with liquid carriers, solid matrices, semi-solid carriers, finely divided solid carriers or combinations thereof, and then, if necessary, introducing or shaping the product into the desired delivery system.

Pharmaceutical formulations containing the agents of the invention can be prepared by procedures known in the art using well known and readily available ingredients. For example, the agent can be formulated with common excipients, diluents, or carriers, including plasma or serum, e.g., patient serum. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols. The formulations can include buffering agents such as calcium carbonate, magnesium oxide and magnesium carbonate, as well as, inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and gelatin, microcrystalline cellulose, sodium lauryl sulfate, starch, talc, or titanium dioxide, or liquid vehicles such as polyethylene glycols (PEGs) and vegetable oil.

The pharmaceutical formulations of the agents of the invention can also take the form of an aqueous or anhydrous solution or dispersion, or alternatively the form of an emulsion or suspension.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

Additionally, the agents are well suited to formulation as sustained release dosage forms and the like. The coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, epicardial patch, leads, and the like.

The formulations and compositions described herein may also contain other ingredients such as antimicrobial agents, or preservatives. Furthermore, as described herein the active ingredients may also be used in combination with other therapeutic agents or therapies.

The cells to be administered may be a population of individual cells or cells grown in culture so as to form a two dimensional or three dimensional structure. The number of cells to be administered will be an amount which results in a beneficial effect to the recipient. For example, from $10^2$ to $10^{10}$, e.g., from $10^3$ to $10^9$, $10^4$ to $10^8$, or $10^5$ to $10^7$, cells can be administered to, e.g., injected, the region of interest, for instance, infarcted and tissue surrounding infarcted tissue. Agents which may enhance cardiac function or stimulate angiogenesis include but are not limited to pyruvate, catecholamine stimulating agents, fibroblast growth factor, e.g., basic fibroblast growth factor, acidic fibroblast growth factor, fibroblast growth factor-4 and fibroblast growth factor-5, epidermal growth factor, platelet-derived growth factor, vascular endothelial growth factor (e.g., $VEGF_{121}$, $VEGF_{145}$, $VEGF_{165}$, $VEGF_{189}$ or $VEGF_{206}$), tissue growth factors and the like. Such agents may optionally be present in a composition comprising the donor cells or administered separately.

The cells are administered during a prophylactic, diagnostic or therapeutic vascular procedure or an invasive or minimally invasive surgical procedure. In one embodiment, the cells are administered post-MI, within hours, e.g., 1 to 12 hours, to days, e.g., 1 to 2 days, and up to one or more weeks after MI. Preferably, the administration of donor cells is prior to scar formation. The cells may be administered intravenously, transvenously, intramyocardially or by any other convenient route, and delivered by a needle, catheter, e.g., a catheter which includes an injection needle or infusion port, or other suitable device.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed:

1. A method, comprising:
   applying neural electrical stimulation via an implanted device to an efferent parasympathetic neural pathway which innervates a cardiac region in a mammal in need of cardiac repair or enhanced function, wherein the cardiac region is subjected to exogenous cell therapy comprising donor cells, gene therapy and/or cytokine therapy, and the electrical stimulation to the efferent parasympathetic neural pathway is in an amount effective to locally modulate cardiac contractility, locally reduce inflammation, locally reduce mechanical loading, or a combination thereof, in the cardiac region subjected to exogenous cell therapy comprising donor cells, gene therapy and/or cytokine therapy.

2. The method of claim 1 further comprising applying electrical therapy to cardiac tissue.

3. The method of claim 2 wherein the electrical therapy is pacing therapy.

4. The method of claim 2 wherein the electrical therapy is cardiac resynchronization therapy (CRT).

5. The method of claim 3 wherein the electrical therapy is cardioversion/ defibrillation shocks.

6. The method of claim 1 wherein the stimulation is applied to a pathway that includes the vagus nerve, carotid sinus nerve or aortic nerve.

7. The method of claim 1 wherein the vagus nerve is electrically stimulated.

8. The method of claim 1 wherein one or more cardiac fat pads are electrically stimulated.

9. The method of claim 1 wherein the donor cells are stem cells.

10. The method of claim 1 wherein the donor cells are hematopoietic stem cells, bone marrow derived stem cells, neural stem cells, SP cells, bone marrow cells or skeletal myoblasts.

11. The method of claim 1 wherein the donor cells are cultured in vitro prior to subjecting the mammal to cell therapy.

12. The method of claim 1 wherein the donor cells include autologous or allogeneic cells.

13. The method of claim 11 or 12 wherein the donor cells are subjected to hypoxic conditions in vitro prior to implantation.

14. The method of claim 1 wherein the donor cells are genetically modified donor cells.

15. The method of claim 1 wherein the cytokine therapy enhances cell localization and/or proliferation in cardiac tissue.

16. The method of claim 1 wherein the electrical stimulation is provided by a neural stimulation device.

17. The method of claim 16 wherein the stimulation is about 5 to 10 second bursts at burst intervals ranging from approximately 1 burst every 30 seconds to approximately 1 burst every 60 seconds at about a frequency of 5 to 150 Hz.

18. The method of claim 1 wherein the electrical stimulation is provided by a neural stimulation lead connected to a cardiac rhythm management (CRM) device.

19. The method of claim 18 wherein the neural stimulation lead is in a vessel proximal to the neural stimulation site.

20. The method of claim 19 wherein the stimulation is about 5 to 10 second bursts at burst intervals ranging from approximately 1 burst every 30 seconds to approximately 1 burst every 60 seconds at about a frequency of 5 to 150 Hz.

21. The method of claim 20 wherein the CRM comprises a sensor to sense a physiological parameter for cardiac function and to provide a signal indicative of the physiological signal.

22. The method of claim 1 further comprising administering an agent that enhances stem cell localization, survival, proliferation, differentiation, or function in cardiac tissue.

23. The method of claim 1 further comprising administering an agent that enhances cardiac function or angiogenesis.

24. The method of claim 1 wherein the electrical stimulation is applied in response to impaired cardiac function.

25. A method, comprising:
applying neural electrical stimulation therapy via an implanted device using a lead to an efferent parasympathetic neural pathway which innervates a cardiac region in a mammal in need of cardiac repair or enhanced function, which cardiac region is subjected to exogenous cell therapy comprising donor cells, gene therapy and/or cytokine therapy;
sensing a physiologic parameter indicative of local cardiac contractility, local inflammation, local mechanical remodeling, and/or local mechanical loading; and
modifying the neural electrical stimulation therapy based on the sensed physiological parameter.

26. The method of claim 25 wherein the lead emerges from the implantable device, the method further comprising pacing the heart using the lead.

27. The method of claim 26 wherein the lead emerges from the implantable device, the method further comprising pacing the heart using a second lead from the implantable device.

28. The method of claim 25 wherein modifying the therapy includes modulating an amplitude of a stimulation signal.

29. The method of claim 25 wherein modifying the therapy includes modulating a frequency of a stimulation signal.

30. The method of claim 25 wherein modifying the therapy includes modulating a burst frequency of a stimulation signal.

31. The method of claim 25 wherein modifying the therapy includes modulating a duration of a stimulation signal.

32. The method of claim 25 further comprising applying electrical therapy to cardiac tissue.

33. The method of claim 32 wherein the electrical therapy is pacing therapy.

34. The method of claim 32 wherein the electrical therapy is cardiac resynchronization therapy (CRT).

35. The method of claim 32 wherein the electrical therapy is cardioversion/ defibrillation shocks.

36. The method of claim 25 wherein neural electrical stimulation therapy is applied to a pathway that includes the vagus nerve, carotid sinus nerve, aortic nerve, or cardiac fat pads.

37. The method of claim 25 wherein the donor cells are stem cells.

38. The method of claim 1 or 25 further comprising administering a drug.

* * * * *

UNITED STATES PATENT AND TRADEMARK OFFICE
CERTIFICATE OF CORRECTION

PATENT NO. : 7,548,780 B2
APPLICATION NO. : 11/063170
DATED : June 16, 2009
INVENTOR(S) : Imad Libbus et al.

It is certified that error appears in the above-identified patent and that said Letters Patent is hereby corrected as shown below:

In column 6, line 53, delete "ending" and insert -- endings --, therefor.

In column 9, line 45, after "as" delete "hematepeetie".

In column 9, line 56, delete "10second" and insert -- 10 second --, therefor.

In column 9, line 57, delete "redetermined" and insert -- predetermined --, therefor.

In column 9, line 64, delete "patients" and insert -- patient --, therefor.

In column 10, line 56, delete "embyronic" and insert -- embryonic --, therefor.

In column 10, line 67, delete "Circulation 104 1-207" and insert -- Circulation, 104, I-207 --, therefor.

In column 11, line 1, delete "111-210" and insert -- III-210 --, therefor.

In column 11, line 2, delete "Res" and insert -- Res., --, therefor.

In column 11, line 10, delete "5,543,318discusses" and insert -- 5,543,318 discusses --, therefor.

In column 11, line 13, delete "5,486,359discusses" and insert -- 5,486,359 discusses --, therefor.

In column 11, line 28, delete ""the" and insert -- " the --, therefor.

In column 11, line 32, delete "viral- mediated" and insert -- viral-mediated --, therefor.

In column 14, line 33, delete "C. Biological Conditioning" and insert the same above "Biological Conditioning" on Col. 14, Line 33, as a heading to the text.

In column 14, line 56, delete "beta- MyHC" and insert -- beta-MyHC --, therefor.

In column 14, line 57, delete "Res 78" and insert -- Res., 78, --, therefor.

In column 14, line 63, delete "acidic - FGF" and insert -- acidic-FGF --, therefor.

In column 14, line 64, delete "FGF-8and FGF -9" and insert -- FGF-8 and FGF-9 --, therefor.

In column 14, line 66, delete "$VEGF_{12O}$" and insert -- $VEGF_{120}$ --, therefor.

In column 14, line 67, delete "$VEGF_{2O6}$" and insert -- $VEGF_{206}$ --, therefor.

CERTIFICATE OF CORRECTION (continued)  Page 2 of 4
U.S. Pat. No. 7,548,780 B2

In column 15, line 5, delete "GATA-4and dHAND/eHAiND)," and insert -- GATA-4 and dHAND/eHAND), --, therefor.

In column 15, line 7, delete "2or" and insert -- 2 or --, therefor.

In column 15, line 8, delete "IGF 1" and insert -- IGF-1 --, therefor.

In column 15, line 16, delete "cylase" and insert -- cyclase --, therefor.

In column 15, line 17, delete "adenyl cylase" and insert -- adenylyl cyclase --, therefor.

In column 15, lines 25-26, delete "HSP60,α-1antitrypsin, HF-1a , HF-1b ," and insert -- HSP60, α-1 antitrypsin, HF-1a, HF-1b, --, therefor.

In column 15, line 27, delete "BMP -17" and insert -- BMP-17 --, therefor.

In column 15, lines 31-32, delete "α,β,γ or δsarcoglycan" and insert -- α, β, γ, or δ sarcoglycan --, therefor.

In column 15, line 33, delete "130receptor" and insert -- 130 receptor --, therefor.

In column 15, line 33, delete "A3receptor" and insert -- A3 receptor --, therefor.

In column 15, line 36, delete "anti -apoptosis" and insert -- anti-apoptosis --, therefor.

In column 15, line 43, delete "HIF - 1α" and insert -- HIF-1α --, therefor.

In column 15, line 49, delete "KCNQ 1" and insert -- KCNQ1 --, therefor.

In column 15, line 51, delete "Kir6.1and" and insert -- Kir6.1 and --, therefor.

In column 15, line 56, delete "factor-a" and insert -- factor-α --, therefor.

In column 15, line 57, delete "factor - β" and insert -- factor-β --, therefor.

In column 15, lines 63-64, after "gene product." delete "gene product, or encodes an inhibitor of the gene product.".

In column 17, line 50, delete "VEGE" and insert -- VEGF --, therefor.

In column 17, line 51, delete "VEGF$_{12O}$" and insert -- VEGF$_{120}$ --, therefor.

In column 17, line 52, delete "VEGF$_{2O6}$" and insert -- VEGF$_{206}$ --, therefor.

In column 17, line 52, delete "TGF -beta" insert -- TGF-beta --, therefor.

In column 17, line 55, delete "GATA-4and" and insert -- GATA-4 and --, therefor.

CERTIFICATE OF CORRECTION (continued)
U.S. Pat. No. 7,548,780 B2

In column 17, line 64, delete "adenyl cylase" and insert -- adenylyl cyclase --, therefor.

In column 17, line 65, delete "V2vasopressin" and insert -- V2 vasopressin --, therefor.

In column 17, lines 65-66, delete "phospholamban ,β-adrenergic" and insert -- phospholamban, β-adrenergic --, therefor.

In column 18, line 4, delete "α1" and insert -- α-1 --, therefor.

In column 18, line 9, delete "α,β,γ" and insert -- α, β, γ --, therefor.

In column 18, line 11, delete "A3receptor" and insert -- A3 receptor --, therefor.

In column 18, line 12, delete "angiogenin-1or" and insert -- angiogenin-1 or --, therefor.

In column 18, line 14, delete "ERK type" and insert -- ERK-type --, therefor.

In column 18, line 14, delete "(p42and" and insert -- (p42 and --, therefor.

In column 18, line 20, delete "5azacytidine" and insert -- 5 azacytidine --, therefor.

In column 18, lines 44-61, Below "in their entirety." delete "The amount of agent administered, including cells, gene therapy vectors and/or one or more cytokines which are exogenously administered, and including agents released from a device, in conjunction with electrical therapies described herein, will vary depending on various factors including, but not limited to, the agent chosen, the disease, whether prevention or treatment is to be achieved, and if the agent is modified for bioavailability and in vivo stability. Thus, the agents of the invention may be employed in conjunction with other therapies, e.g., therapies for ischemia or arrhythmias, including gene therapies and/or cell therapies, e.g., see U.S. patent application Ser. No. 10/723,258, filed on Nov. 25, 2003, entitled "METHOD AND APPARATUS FOR CELL AND ELECTRICAL THERAPY OF LIVING CELLS" and U.S. patent application Ser. No. 10/788,906, filed on Feb. 27, 2004, entitled "METHOD AND APPRATUS FOR DEVICE CONTROLLED GENE EXPRESSION", the disclosures of which are incorporated herein by reference in their entirety.".

In column 21, line 6, in Claim 5, delete "cardioversion/ defibrillation" and insert -- cardioversion/defibrillation --, therefor.

In column 22, line 42, in Claim 35, delete "cardioversion/ defibrillation" and insert -- cardioversion/defibrillation --, therefor.

Signed and Sealed this

Ninth Day of February, 2010

David J. Kappos
*Director of the United States Patent and Trademark Office*